US010958852B2

(12) United States Patent
Fukumoto

(10) Patent No.: US 10,958,852 B2
(45) Date of Patent: Mar. 23, 2021

(54) IMAGING APPARATUS AND CONTROL METHOD HAVING A PLURALITY OF SYNCHRONIZED LIGHT SOURCE DEVICES

(71) Applicant: CANON KABUSHIKI KAISHA, Tokyo (JP)

(72) Inventor: Junya Fukumoto, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/582,211

(22) Filed: Sep. 25, 2019

(65) Prior Publication Data

US 2020/0128166 A1    Apr. 23, 2020

(30) Foreign Application Priority Data

Oct. 19, 2018 (JP) ................................ 2018-197934

(51) Int. Cl.
*H04N 5/235* (2006.01)
*A61B 1/00* (2006.01)
(Continued)

(52) U.S. Cl.
CPC ......... *H04N 5/2354* (2013.01); *A61B 1/0002* (2013.01); *A61B 1/00009* (2013.01); *A61B 1/00195* (2013.01); *A61B 1/043* (2013.01); *A61B 1/045* (2013.01); *A61B 1/0646* (2013.01); *A61B 1/0661* (2013.01);
(Continued)

(58) Field of Classification Search
CPC .. H04N 5/2354; H04N 5/2353; H04N 5/2351; H04N 2005/2255; A61B 1/00195; A61B 1/0661; A61B 1/0646; A61B 1/043; A61B 1/0002; A61B 1/0684;
(Continued)

(56) References Cited

U.S. PATENT DOCUMENTS 8,858,429 B2 * 10/2014 Mizuyoshi ............. A61B 1/063
600/180
9,949,625 B2 *  4/2018 Fukuda .................... A61B 1/04
(Continued)

FOREIGN PATENT DOCUMENTS

JP        6019167 B1    11/2016
JP      2018-175871 A   11/2018
WO   WO 2014/125724 A1   8/2014

OTHER PUBLICATIONS

U.S. Appl. No. 15/952,916, filed Apr. 13, 2018, 2018/0302584 A1, Fukumoto, J, et al.

*Primary Examiner* — Luong T Nguyen
(74) *Attorney, Agent, or Firm* — Venable LLP

(57) ABSTRACT

An imaging apparatus according to an embodiment includes a first light source which emits first light, a second light source which emits second light, an imaging sensor, and control circuitry. The image sensor includes a plurality of pixels to receive light from an object, reads an electric signal generated by the pixel with a rolling shutter method, and outputs the electric signal for each frame. The control circuitry causes the first light source to be turned on M (M is an integer equal to or less than N) times in N frames in synchronization with a first period based on a blanking period of the frame, and causes the second light source to be turned on by selectively using multiple lighting patterns in which lighting timing is set in synchronization with the first period and a total lighting period in the N frames is different.

11 Claims, 9 Drawing Sheets

(51) Int. Cl.
  *A61B 1/06* (2006.01)
  *A61B 1/04* (2006.01)
  *A61B 1/045* (2006.01)
  *H04N 5/225* (2006.01)

(52) U.S. Cl.
  CPC ......... *A61B 1/0684* (2013.01); *H04N 5/2351* (2013.01); *H04N 5/2353* (2013.01); *H04N 2005/2255* (2013.01)

(58) Field of Classification Search
  CPC . A61B 1/00009; A61B 1/045; A61B 1/00006; A61B 1/00186
  See application file for complete search history.

(56) References Cited

U.S. PATENT DOCUMENTS

| | | | |
|---|---|---|---|
| 10,051,193 B2* | 8/2018 | Kagawa | A61B 1/04 |
| 2013/0050456 A1* | 2/2013 | Sakurai | H04N 5/2354 348/68 |
| 2013/0158352 A1* | 6/2013 | Imaizumi | A61B 1/00009 600/111 |
| 2015/0022647 A1 | 1/2015 | Takei et al. | |
| 2016/0317003 A1 | 11/2016 | Ogata et al. | |
| 2018/0302584 A1 | 10/2018 | Fukumoto et al. | |

\* cited by examiner

IMAGING APPARATUS AND CONTROL METHOD HAVING A PLURALITY OF SYNCHRONIZED LIGHT SOURCE DEVICES

CROSS-REFERENCE TO RELATED APPLICATIONS

This application is based upon and claims the benefit of priority from Japanese Patent Application No. 2018-197934, filed on Oct. 19, 2018; the entire contents of which are incorporated herein by reference.

FIELD

Embodiments described herein relate generally to an imaging apparatus and a control method.

BACKGROUND

For imaging apparatuses such as endoscope apparatuses, CCD (Charge Coupled Device) image sensors used to be primarily used; however, in recent years, CMOS (Complementary Metal Oxide Semiconductor) image sensors have been dominant because they offer advantages in a reduction in costs, a single power source, low power consumption, etc. For CMOS image sensors, typically, a rolling shutter method is often used.

DETAILED DESCRIPTION

An imaging apparatus according to an embodiment includes a first light source, a second light source, an imaging sensor, and control circuitry. The first light source emits first light. The second light source emits second light having a wavelength band that is partly or wholly different from a wavelength band of the first light. The image sensor includes a plurality of pixels arranged in a matrix to receive light from an object irradiated with the first light and the second light, reads an electric signal generated by the pixel with a rolling shutter method, and outputs the electric signal for each frame. The control circuitry causes the first light source to be turned on M (M is an integer equal to or less than N (N is an integer equal to or more than two)) times in N frames in synchronization with a first period based on a blanking period of the frame, and causes the second light source to be turned on by selectively using multiple lighting patterns in which lighting timing is set in synchronization with the first period and a total lighting period in the N frames is different.

With reference to drawings, an imaging apparatus and a control method according to an embodiment are described below. The embodiment is not limited to the details described below. In principle, the details described in an embodiment or modifications are also applied to other embodiments or modifications.

Figure 1:
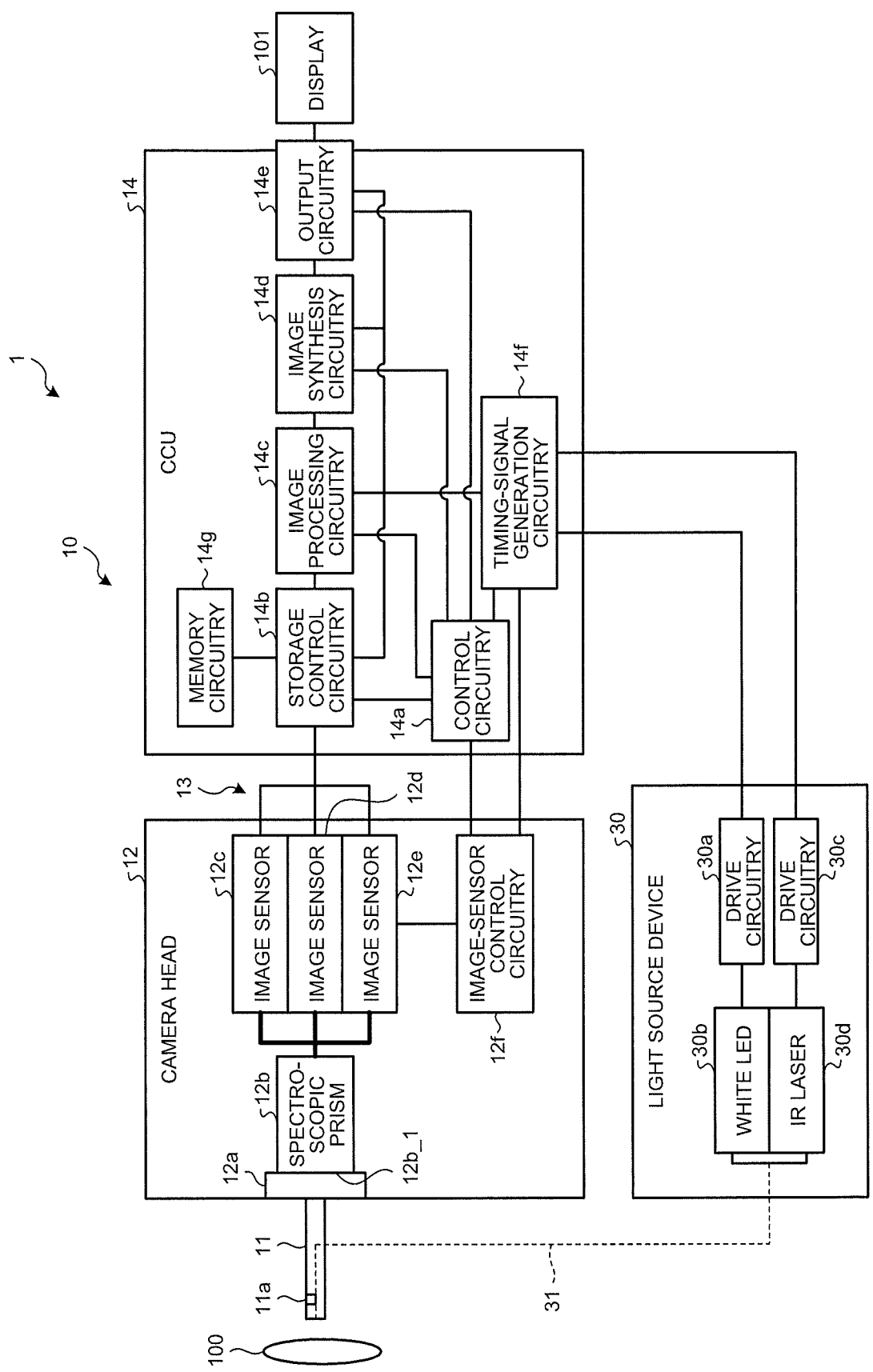
FIG. 1 is a diagram that illustrates an example of the configuration of an imaging system including an imaging apparatus according to an embodiment.

FIG. 1 is a diagram that illustrates an example of the configuration of an imaging system 1 including an imaging apparatus 10 according to the present embodiment. As illustrated in FIG. 1, the imaging system 1 according to the present embodiment includes the imaging apparatus 10, a light source device 30, and an optical fiber 31.

The imaging apparatus 10 is, for example, an apparatus that is used as a rigid medical endoscope and that captures the inside of the body of a subject 100. The imaging apparatus 10 includes a scope 11, a camera head 12, a camera cable 13, and a CCU (Camera Control Unit) 14.

The scope 11 is inserted into the body of the subject 100 when imaging is conducted. An objective lens 11a is provided at the distal end of the scope 11. The scope 11 is rigid so as not to be bent.

The camera head 12 includes an excitation-light cut filter 12a, a spectroscopic prism 12b, three image sensors 12c to 12e (12c, 12d, 12e), and image-sensor control circuitry 12f.

The excitation-light cut filter 12a is an optical device that is provided by being opposed to imaging areas of pixels and that causes the pixels to receive light other than the excitation light output from the light source device 30. The excitation-light cut filter 12a is a filter that is provided between the scope 11 and an incidence plane 12b 1 of the spectroscopic prism 12b to cut excitation light from the light entering from the objective lens 11a and allows passage of light other than the excitation light. Therefore, the incidence plane 12b 1 of the spectroscopic prism 12b receives light other than excitation light, included in reflected light (returning light) of the light emitted to body tissues of the subject 100 by the light source device 30. In the following description, reflected light of white light entering the spectroscopic prism 12b and then entering the image sensor 12c is sometimes simply referred to as white light.

The spectroscopic prism 12b disperses incident light into red (R) light, green (G) light, and blue (B) light. Then, the spectroscopic prism 12b focuses blue light onto the imaging surface of the image sensor 12c. The spectroscopic prism 12b focuses green light onto the imaging surface of the image sensor 12d. The spectroscopic prism 12b focuses red light onto the imaging surface of the image sensor 12e.

Each of the image sensors 12c to 12e is, for example, a CMOS (Complementary Metal Oxide Semiconductor) image sensor. The image sensors 12c to 12e are provided such that the imaging surface of each of the image sensors 12c to 12e substantially matches the image formation surface of the spectroscopic prism 12b. The pixels in each of the three (multiple) image sensors 12c to 12e output video signals when they receive the corresponding type of light.

Each of the image sensors 12c to 12e includes a plurality of pixels (imaging elements). The pixels are arranged in a matrix on an imaging surface. Due to drive control by the image-sensor control circuitry 12f, each pixel receives light to generate a video signal (electric signal) and outputs the generated video signal. For example, each pixel of the image sensor 12c receives blue light to output a B signal (B video signal). Each pixel of the image sensor 12d receives green light to output a G signal (G video signal). Each pixel of the image sensor 12e receives red light to output an R signal (R video signal). For example, the camera head 12 including the image sensors 12c to 12e outputs an RGB signal to the CCU 14 via the camera cable 13. The image sensors 12c to 12e output an analog video signal.

Here, the imaging apparatus 10 is used for, for example, surgical operation conducted on the subject 100 with ICG (indocyanine green) fluorescence angiography. According to the present embodiment, ICG is administered into the subject 100. ICG is excited by excitation light output from an IR laser 30d to generate near-infrared fluorescence (hereafter, referred to as fluorescence) of approximately 800 to 850 nm. The fluorescence passes through the excitation-light cut filter 12a and is focused on the imaging surface of the image sensor 12e by the spectroscopic prism 12b. That is, the image sensor 12e receives fluorescence based on excitation light and then outputs an R signal. In the following description, the image sensor 12e receives fluorescence and the imaging apparatus 10 performs various operations; however, without providing the excitation-light cut filter 12a, the imaging apparatus 10 may cause the image sensor 12e to receive reflected light of the excitation light and perform the same operation.

Each of the image sensors 12c to 12e is a rolling-shutter type image sensor that, on a frame-to-frame (image) basis, repeatedly performs a process to sequentially start to conduct exposure on at least every line, starting from the first line of pixels to the last line, and output a video signal sequentially from the line for which exposure has finished. Here, the exposure means for example the storage of electric charge in a pixel.

Instead of the spectroscopic prism 12b and the three image sensors 12c to 12e, the camera head 12 may include a Bayer filter and a single image sensor. In this case, a Bayer filter is provided at the side of the imaging surface of the image sensor such that each pixel is opposed to any of the red filter, the green filter, and the blue filter. Thus, one pixel corresponds to one color filter. On a pixel by pixel basis, the image sensor outputs a video signal in the color of the filter corresponding to the pixel. Furthermore, on a pixel by pixel basis, image processing circuitry 14c described later performs an estimation process to estimate video signals in the remaining two colors, which are difficult to be directly obtained, on the basis of video signals output from neighboring pixels of the pixel. As a result, the imaging apparatus 10 may obtain an RGB signal as a video signal for each pixel.

The image-sensor control circuitry 12f controls driving of the image sensors 12c to 12e on the basis of a control signal output from control circuitry 14a described later and various synchronization signals output from timing-signal generation circuitry 14f described later. For example, on the basis of the control signal and the various synchronization signals, the image-sensor control circuitry 12f controls the image sensors 12c to 12e so as to perform a gain amplification process (analog gain amplification process) to amplify gain with regard to analog video signals output from the image sensors 12c to 12e and output the gain-amplified video signals to the CCU 14. Alternatively, in a case where the image sensors 12c to 12e include an undepicted AD converter, the image-sensor control circuitry 12f controls the image sensors 12c to 12e so as to perform a gain amplification process (digital gain amplification process) to amplify the gain with regard to digital video signals output from the image sensors 12c to 12e and output the video signals with the gain amplified to the CCU 14.

The camera cable 13 is a cable that contains a signal line for transmitting and receiving a video signal, a control signal, and a synchronization signal between the camera head 12 and the CCU 14.

The CCU 14 performs various types of image processing on a video signal output from the camera head 12 to generate image data representing the image to be displayed on a display 101 and outputs the image data to the display 101 coupled to the CCU 14. A video signal on which various types of image processing has been conducted is the image data representing the image to be displayed on the display 101.

The CCU 14 includes the control circuitry 14a, storage control circuitry 14b, the image processing circuitry 14c, image synthesis circuitry 14d, output circuitry 14e, the timing-signal generation circuitry 14f, and memory circuitry 14g. In a case where the image sensors 12c to 12e do not include an AD converter, the CCU 14 also includes an undepicted AD (Analog to Digital) converter, or the like. For example, the AD converter converts an analog video signal output from the camera head 12 into a digital video signal.

The control circuitry 14a controls various components of the imaging apparatus 10. For example, the control circuitry 14a outputs a control signal to each circuitry, i.e., the image-sensor control circuitry 12f, the storage control circuitry 14b, the image processing circuitry 14c, the image synthesis circuitry 14d, the output circuitry 14e, and the timing-signal generation circuitry 14f so as to control each circuitry. The control circuitry 14a reads a control program for the imaging apparatus 10, stored in the memory circuitry 14g, and executes the read control program to perform a control process to control various components of the imaging apparatus 10. Alternatively, the control circuitry 14a includes an undepicted internal memory circuitry and executes a control program stored in the memory circuitry. The control circuitry 14a is implemented by using a processor such as an MPU (Micro-processing Unit).

The storage control circuitry 14b performs a control so as to store a video signal, output from the camera head 12, in the memory circuitry 14g in accordance with a control signal output from the control circuitry 14a and various synchronization signals output from the timing-signal generation circuitry 14f. The storage control circuitry 14b reads a video signal stored in the memory circuitry 14g on a per-line basis in accordance with a control signal and a synchronization signal. Then, the storage control circuitry 14b outputs the read video signal of one line to the image processing circuitry 14c.

The image processing circuitry 14c is an example of an amplification circuit. The image processing circuitry 14c performs various types of image processing on a video signal output from the storage control circuitry 14b in accordance with a control signal output from the control circuitry 14a and various synchronization signals output from the timing-signal generation circuitry 14f. Thus, the image processing circuitry 14c generates image data representing the image to be presented on the display 101. That is, the image processing circuitry 14c generates an image on the basis of a video signal.

For example, the image processing circuitry 14c performs a gain amplification process (digital gain amplification process) on a video signal output from the storage control circuitry 14b to adjust the brightness of an image. The image processing circuitry 14c may conduct a noise reduction process to reduce noise, an outline highlight process to highlight an outline, or the like, on a video signal output from the storage control circuitry 14b. Then, the image processing circuitry 14c outputs a video signal on which various types of image processing has been performed (image data representing the image to be presented on the display 101) to the image synthesis circuitry 14d.

On the basis of a control signal output from the control circuitry 14a and various synchronization signals output from the timing-signal generation circuitry 14f, the image synthesis circuitry 14d synthesizes video signals output from the image processing circuitry 14c to generate synthesis image data. Then, the image synthesis circuitry 14d outputs the synthesis image data to the display 101.

For example, the storage control circuitry 14b, the image processing circuitry 14c, and the image synthesis circuitry 14d are implemented by using a single processor such as a DSP (Digital Signal Processor). For example, the storage control circuitry 14b, the image processing circuitry 14c, the image synthesis circuitry 14d, and the timing-signal generation circuitry 14f are implemented by using a single FPGA (Field Programmable Gate Array). The control circuitry 14a, the storage control circuitry 14b, the image processing circuitry 14c, and the image synthesis circuitry 14d may be implemented by using a single processing circuitry. This processing circuitry is implemented by using for example a processor.

The output circuitry 14e outputs synthesis image data, output from the image synthesis circuitry 14d, to the display 101. This allows the display 101 to present the synthesis image represented by the synthesis image data. The synthesis image is an example of an image. The output circuitry 14e is implemented by using, for example, an HDMI (High-Definition Multimedia Interface) (registered trademark) driver IC (Integrated Circuit) or an SDI (Serial Digital Interface) driver IC.

The timing-signal generation circuitry 14f integrally controls various types of timing, such as the output timing of light from the light source device 30, the exposure timing of the image sensors 12c to 12e, the output timing of a video signal, or the control timing of the memory circuitry 14g by the storage control circuitry 14b. The control circuitry 14a and the timing-signal generation circuitry 14f are an example of a control unit.

The timing-signal generation circuitry 14f generates various synchronization signals such as horizontal synchronization signals, vertical synchronization signals, or other synchronization signals for synchronization of the entire imaging apparatus 10 on the basis of clock signals generated by an undepicted oscillation circuitry. Then, the timing-signal generation circuitry 14f outputs various generated synchronization signals to each circuitry, i.e., the image-sensor control circuitry 12f, the control circuitry 14a, the storage control circuitry 14b, the image processing circuitry 14c, the image synthesis circuitry 14d, and the output circuitry 14e.

The timing-signal generation circuitry 14f generates a light-source control signal on the basis of a clock signal and a control signal output from the control circuitry 14a. A light-source control signal is a control signal for controlling light output from the light source device 30 and synchronizing the entire imaging system 1. The timing-signal generation circuitry 14f outputs the generated light-source control signal to the light source device 30.

For example, the waveform of a light-source control signal is a square wave, and a light-source control signal has two levels (states), a high level and a low level. For example, the light-source control signal is a control signal for, in a high level, causing a white LED 30b to output white light and causing the IR laser 30d to output excitation light and, in a low level, causing the white LED 30b to be turned off and causing the IR laser 30d to stop outputting excitation light.

The memory circuitry 14g is implemented by using, for example, a semiconductor memory device such as a RAM (Random Access Memory) or a flash memory, a hard disk, or an optical disk. The memory circuitry 14g stores various programs. For example, the memory circuitry 14g stores a control program executed by the control circuitry 14a. The storage control circuitry 14b temporarily stores a video signal in the memory circuitry 14g.

The light source device 30 outputs white light or excitation light in accordance with a light-source control signal. The light source device 30 includes drive circuitry 30a, the white LED (Light Emitting Diode) 30b, drive circuitry 30c, and the IR laser 30d.

The drive circuitry 30a conducts drive control to drive the white LED 30b so as to be turned on in accordance with a light-source control signal output from the timing-signal generation circuitry 14f. The white LED 30b outputs white light due to the drive control by the drive circuitry 30a. The white light is for example visible light. The while LED 30b is an example of a first light source. The white light is an example of first light.

The drive circuitry 30c conducts drive control to drive the IR laser 30d so as to output excitation light from the IR laser 30d in accordance with a light-source control signal output from the timing-signal generation circuitry 14f. The IR laser 30d outputs excitation light due to the drive control by the drive circuitry 30c. As described above, excitation light is cut by the excitation-light cut filter 12a. Fluorescence (fluorescence based on excitation light), which is output from ICG after ICG is excited by excitation light, is passed through the excitation-light cut filter 12a and is received by the image sensor 12e. The IR laser 30d is an example of a second light source. The excitation light is an example of second light.

According to the present embodiment, the white light output from the white LED 30b and the excitation light output from the IR laser 30d have different wavelength bands; however, this is not a limitation, and the wavelength band of the excitation light and the wavelength band of the white light may be partly overlapped.

The optical fiber 31 guides white light and excitation light from the light source device 30 to the distal end of the scope 11 and causes them to be output from the distal end of the scope 11.

In the imaging apparatus 10 having the above-described configuration, the amount of reflected light of white light output from the white LED 30b and the amount of fluorescence generated due to the emission of excitation light are sometimes unbalanced depending on the distance between the imaging apparatus 10 and the subject 100, the state of illumination around the subject 100, or the like. In such a case, the image (color image) obtained by receiving reflected light of white light and the image (fluorescence image)

obtained by receiving fluorescence based on excitation light have uneven luminance, and therefore there is a problem in that the image quality (luminance) is not sufficient for a user, such as a doctor, who observes the image, e.g., a fluorescence image is too dark as compared with a color image. Furthermore, in this case, a gain amplification process is performed on a fluorescence image so as to improve the luminance of the image; however, as a noise component is also increased in accordance with an increase in the amount of amplification, the frequent use of a gain amplification process may lead to a reduction in the image quality.

Thus, with the above-described configuration, the imaging apparatus 10 further conducts the following operation to ensure the image quality sufficient for the user's observation.

Specifically, the control circuitry 14a performs a control so as to cause the pixels in each of the image sensors 12c to 12e to receive light during only the blanking period or the period centered on the blanking period. For example, the control circuitry 14a outputs a control signal to the image-sensor control circuitry 12f so as to cause the image-sensor control circuitry 12f to perform the above control.

Here, the control circuitry 14a performs control so as to cause the pixels to receive light during a period that is less than the read period. The read period refers to, for example, the period during which video signals of one frame are output from the image sensors 12c to 12e. Furthermore, the read period refers to, for example, the period from when the output of a video signal from the first line in one frame is started until the output of a video signal from the last line is finished.

According to the present embodiment, the blanking period refers to, for example, a period corresponding to the period from when the output of a video signal from the last line of the image sensors 12c to 12e is finished with respect to the imaging for the n-th (n is a positive integer) frame until the output of a video signal from the first line of the image sensors 12c to 12e is started with respect to the imaging for the (n+1)-th frame.

According to the present embodiment, the frame rate of a video signal (image) output from the imaging apparatus 10 to the display 101 is A [fps (frame per second)]. In this case, image sensors that enable a read period of 1/(M·A) [s] are used as the image sensors 12c to 12e of the imaging apparatus 10. That is, image sensors capable of outputting a video signal from each line at an interval of 1/(M·k·A) [s] are used as the image sensors 12c to 12e. Here, "M" is a number larger than one, and "k" is the number of lines of pixels in each of the image sensors 12c to 12e. In the example described below, for example M=2; however, M may be a number different from two and larger than one.

The control circuitry 14a outputs, to the image-sensor control circuitry 12f, a control signal for causing the image sensors 12c to 12e to output video signals of one frame in the read period of 1/(2 A) [s] that is shorter than the exposure period of 1/A [s]. Here, the exposure period refers to, for example, the period from when a pixel starts to store an electric charge until when it ends.

Furthermore, the control circuitry 14a selectively uses multiple output patterns (lighting patterns), in which the output timing (lighting timing) is set in synchronization with the blanking period or the period centered on the blanking period and the total output period (total lighting period) in two frames is different, to control the excitation light output from the IR laser 30d.

An operation of the above-described control circuitry 14a is described in a case where, for example, A=60. That is, in the described case, the exposure period and the period during which video signals of one frame are output from the imaging apparatus 10 to the display 101 are the same, 1/60 [s], and the read period is 1/120 [s].

Figure 2:
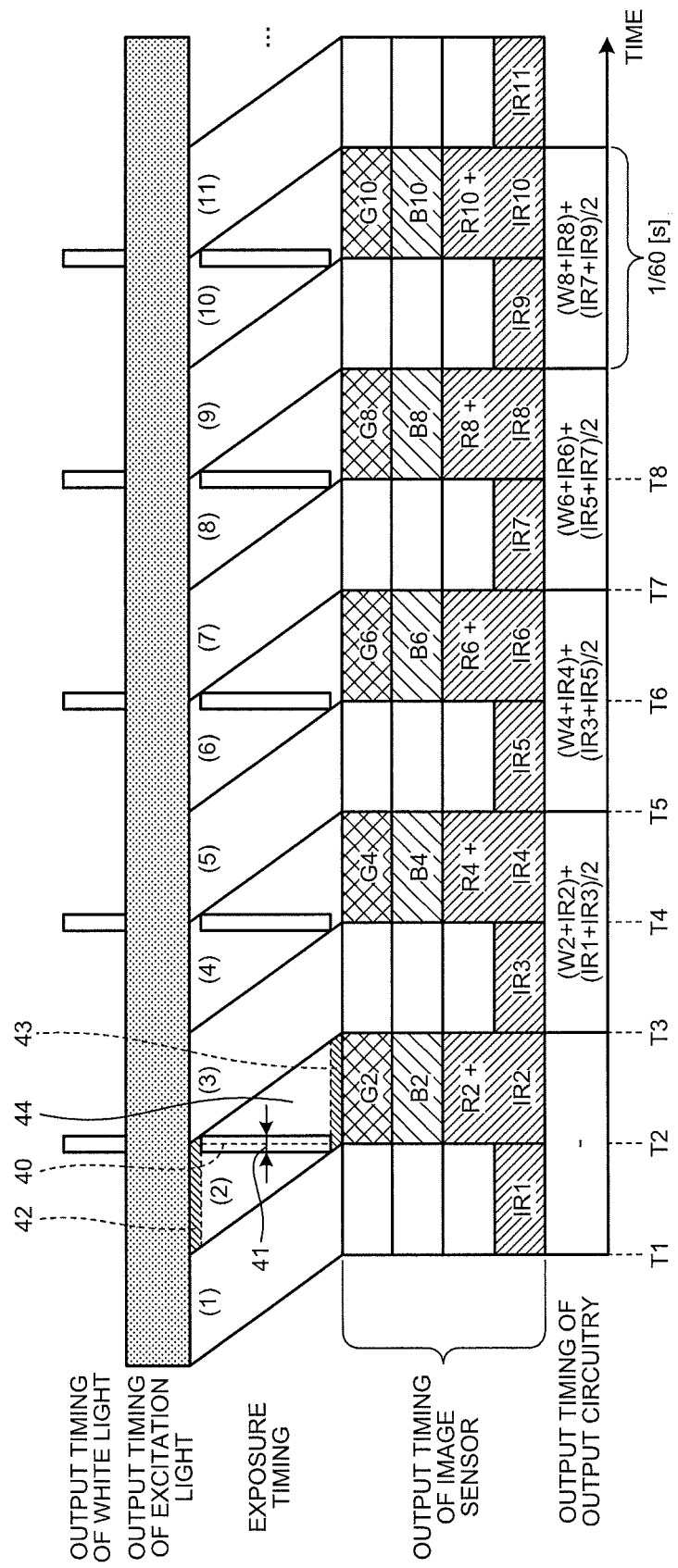
FIG. 2 is a diagram that illustrates an example of an imaging operation of the imaging apparatus according to the embodiment.

First, with reference to FIG. 2, the output pattern is described in a case where the amount of fluorescence generated due to the emission of excitation light is extremely small as compared with the amount of reflected light of the white light output from the white LED 30b.

FIG. 2 is a diagram that illustrates an example of an imaging operation of the imaging apparatus 10. FIG. 2 illustrates an example of the relation among the output timing of white light and excitation light output from the light source device 30, the exposure timing of each line of pixels included in the image sensors 12c to 12e of the imaging apparatus 10, the output timing of video signals output from the image sensors 12c to 12e, and the output timing of a video signal output from the output circuitry 14e. In FIG. 2, the horizontal axis indicates a time. Here, the output timing of excitation light corresponds to the output pattern (lighting pattern) of the IR laser 30d.

In FIG. 2, for simplification of the drawing, two different times, i.e., the time (timing) when the output of a video signal from the last line of the image sensors 12c to 12e is finished with respect to the imaging for the n-th frame and the time when the output of a video signal from the first line in the image sensors 12c to 12e is started with respect to the imaging for the (n+1)-th frame, are represented as the identical "Tp (p=n+1)". In actuality, as described above, a blanking period exists as the period from when the output of a video signal from the last line of the image sensors 12c to 12e is finished with respect to the imaging for the n-th frame to when the output of a video signal from the first line of the image sensors 12c to 12e is started with respect to the imaging for the (n+1)-th frame.

In FIG. 2, (n) indicates the exposure timing during the imaging for the n-th frame. Here, n is a positive integer as described above. When n is an odd number, IRn denotes the R signal output from the image sensor 12e with regard to the imaging for the n-th frame. That is, when n is an odd number, IRn denotes the R signal output from the image sensor 12e that has received fluorescence based on excitation light.

Conversely, when n is an even number, Gn denotes the G signal output from the image sensor 12d with regard to the imaging for the n-th frame. When n is an even number, Bn denotes the B signal output from the image sensor 12c with regard to imaging for the n-th frame. When n is an even number, "Rn+IRn" denotes the R signal output from the image sensor 12e with regard to the imaging for the n-th frame. Specifically, "Rn+IRn" denotes the R signal output from the image sensor 12e that has simultaneously received white light and fluorescence based on excitation light with regard to the imaging for the n-th frame. Furthermore, "Wn+IRn" denotes the RGB signal output from the image sensors 12c to 12e with regard to the imaging for the n-th frame. That is, "Wn+IRn" is a synthesis signal of Gn, Bn, and Rn.

In the example of FIG. 2, before the imaging for the first frame is started or when the imaging for the first frame is started, the control circuitry 14a outputs, to the timing-signal generation circuitry 14f, a control signal for outputting a first light-source control signal. The first light-source control signal is a control signal for implementing an output pattern (first lighting pattern) that causes the IR laser 30d to continuously output excitation light.

The timing-signal generation circuitry 14f outputs, to the drive circuitry 30c, the first light-source control signal for continuously outputting excitation light on the basis of the above-described control signal output from the control circuitry 14a. The drive circuitry 30c causes the IR laser 30d to continuously output excitation light on the basis of the first light-source control signal output from the timing-signal generation circuitry 14f.

As illustrated in FIG. 2, during the imaging for the first frame, the exposure is sequentially started on a per-line basis, starting from the first line of pixels to the last line. With respect to the imaging for the first frame, fluorescence based on excitation light is received by the image sensor 12e, and the image sensor 12e outputs the R signal (IR1) during the read period of $1/120$ [s] from a time T1 to a time T2. That is, the image sensor 12e outputs a video signal from each line at the interval of $1/(120 \text{ k})$ [s]. The time T1 is a time when the output of a video signal from the first line is started with regard to the first frame. The time T2 is a time when the output of a video signal from the last line is finished with regard to the first frame.

A specific control method is described; the control circuitry 14a outputs, to the image-sensor control circuitry 12f, the control signal for causing the image sensor 12e to output video signals of the first frame during the read period of $1/120$ [s] from the time T1. Specifically, the control circuitry 14a outputs, to the image-sensor control circuitry 12f, the control signal for causing the image sensor 12e to start to sequentially output a video signal from each line at the interval of $1/(120 \text{ k})$ [s] from the time T1.

The image-sensor control circuitry 12f controls the image sensor 12e so as to be driven on the basis of the control signal. As a result, the image sensor 12e outputs video signals from all the lines (k lines) during the read period of $1/120$ [s] from the time T1 to the time T2.

Then, each time a video signal output from each line of the image sensor 12e is input with respect to the imaging for the first frame, the storage control circuitry 14b temporarily stores the video signal output from each line in the memory circuitry 14g. Here, from the time T1 to the time T2, the storage control circuitry 14b stores a video signal output from each line, sequentially from the first line to the last line, in the memory circuitry 14g. Video signals stored with respect to the imaging for the first frame as described above are stored in the memory circuitry 14g until at least a time T5.

Then, as illustrated in FIG. 2, during the imaging for the second frame, the exposure is sequentially started on a per-line basis from the first line of the pixels in each of the image sensors 12c to 12e to the last line.

Here, the period from the time T2 when the output of a video signal from the last line is finished with regard to the imaging for the first frame to the time when the output of a video signal from the first line is started with regard to the imaging for the second frame corresponds to a blanking period 40, as illustrated in FIG. 2. As the blanking period 40 is a relatively short period as compared with an exposure period, or the like, it is indicated by a single dotted line in FIG. 2; however, in actuality, it is a period that has a certain width in the direction of a time axis.

According to the present embodiment, as illustrated in FIG. 2, with regard to the imaging for the second frame, white light is output from the white LED 30b during the blanking period 40 or a period 41 (hereafter, referred to as blanking peripheral period) centered on the blanking period 40. For example, in a case where white light is output during only the blanking peripheral period 41, at least one line 42 at the side of the first line and at least one line 43 at the side of the last line among all the lines of pixels in the image sensors 12c to 12e are irradiated with white light in only a time shorter than the blanking peripheral period 41 with regard to the imaging for the second frame.

The white light may be output from the white LED 30b within the blanking period 40. In this case, the white light may be output at any timing within the blanking period 40. For example, the blanking peripheral period 41 is a period longer than the blanking period 40, and it includes the blanking period 40 and includes periods before and after the blanking period 40. The blanking period 40, a period within the blanking period 40, and the blanking peripheral period 41 centered on the blanking period 40 are examples of a first period based on the blanking period 40.

As illustrated in FIG. 2, the light receiving period for receiving white light is substantially identical for one or more lines 44 except for the line 42 and the line 43 among all the lines. That is, the light receiving period of the line 44 is different from those of the line 42 and the line 43. For this reason, the imaging apparatus 10 masks the image obtained in accordance with video signals output from the line 42 and the line 43 and sets the area of the image obtained in accordance with a video signal output from the line 44 as an effective image area. This allows the display 101 to present an image by masking parts where uneven brightness likely to occur. Therefore, the occurrence of distortion in an image may be prevented. Thus, with the imaging apparatus 10, it is possible to ensure the image quality sufficient for observation to users such as doctors who observe images.

Furthermore, as illustrated in FIG. 2, with regard to the imaging for the third frame, at least one line at the side of the first line among all the lines of pixels receives not only fluorescence based on excitation light but also white light during the exposure period. Furthermore, during the imaging for the first frame, at least one line at the side of the last line among all the lines of pixels receives not only fluorescence based on excitation light but also white light during the exposure period. As a component of white light is thus included, it is difficult to generate a fluorescence image formed of only a fluorescence component with a desired image quality from video signals output from the lines that receive white light as well as fluorescence.

Therefore, with regard to the imaging for the first frame and the imaging for the third frame, too, the imaging apparatus 10 according to the present embodiment masks images obtained in accordance with video signals output from the line 42 and the line 43 and sets the area of the image obtained in accordance with a video signal output from the line 44 as an effective image area. This allows the display 101 to present an image by masking parts whose image quality may be undesirable. Therefore, in this aspect, too, with the imaging apparatus 10, it is possible to ensure the image quality sufficient for observation to users such as doctors who observe images.

Here, an explanation is given of an example of the reason why the blanking peripheral period 41 is a period centered on the blanking period 40. If the blanking peripheral period 41 is not a period centered on the blanking period, there is a possibility that, with regard to an image with its ends masked, the size of the masked area at one end side is different from the size of the masked area at the other end side and a user observing the image may feel uncomfortable.

However, if the blanking peripheral period 41 is a period centered on the blanking period 40, the size of the masked area at one end side substantially matches the size of the masked area at the other end side, and the user's uncomfortable feeling may be prevented.

The image sensors 12c to 12e output video signals (RGB signals) from all the lines (k lines) during the read period of $1/120$ [s] from the time T2 to a time T3.

A specific control method is described. The control circuitry 14a outputs, to the image-sensor control circuitry 12f, the control signal for causing the image sensors 12c to 12e to output video signals during the read period of $1/120$ [s] from the time T2. Specifically, the control circuitry 14a outputs, to the image-sensor control circuitry 12f, the control signal for causing the image sensors 12c to 12e to start to output a video signal from each line at the interval of $1/(120k)$ [s] from the time T2.

In accordance with the control signal, the image-sensor control circuitry 12f controls the driving of the image sensors 12c to 12e. As a result, the image sensor 12c outputs video signals (B signals) from all the lines (k lines) during the read period of $1/120$ [s] from the time T2 to the time T3. The image sensor 12d outputs video signals (G signals) from all the lines (k lines) during the read period of $1/120$ [s] from the time T2 to the time T3. The image sensor 12e outputs video signals (R signals (R2+IR2)) from all the lines (k lines) with regard to the imaging for the second frame during the read period of $1/120$ [s] from the time T2 to the time T3.

Each time a video signal output from each line of the image sensor 12c is input from the time T2 to the time T3, the storage control circuitry 14b temporarily stores the video signal output from each line in the memory circuitry 14g. Furthermore, each time a video signal output from each line of the image sensor 12d is input from the time T2 to the time T3, the storage control circuitry 14b temporarily stores the video signal output from each line in the memory circuitry 14g. Each time a video signal output from each line of the image sensor 12e is input from the time T2 to the time T3, the storage control circuitry 14b temporarily stores the video signal output from each line in the memory circuitry 14g. Here, with regard to the imaging for the second frame, a video signal output from each line, sequentially from the first line to the last line, is stored in the memory circuitry 14g from the time T2 to the time T3. In this manner, video signals stored with regard to the imaging for the second frame are stored in the memory circuitry 14g until at least the time T5.

Then, as illustrated in FIG. 2, during the imaging for the third frame, the exposure is sequentially started on a per-line basis from the first line of the pixels to the last line. With respect to the imaging for the third frame, the image sensor 12e receives fluorescence based on excitation light, and the image sensor 12e outputs an R signal (IR3) during the read period of $1/120$ [s] from the time T3 to a time T4. That is, a video signal is output from each line of the image sensor 12e at the interval of $1/(120k)$ [s]. The time T3 is a time when the output of a video signal from the first line is started with regard to the imaging for the third frame. The time T4 is a time when the output of a video signal from the last line is finished with regard to the imaging for the third frame.

A specific control method is described; the control circuitry 14a outputs, to the image-sensor control circuitry 12f, the control signal for causing the image sensor 12e to output a video signal during the read period of $1/120$ [s] from the time T3. Specifically, the control circuitry 14a outputs, to the image-sensor control circuitry 12f, the control signal for causing the image sensor 12e to start to output a video signal from each line at the interval of $1/(120k)$ [s] from the time T3.

The image-sensor control circuitry 12f controls the driving of the image sensor 12e in accordance with the control signal. As a result, the image sensor 12e outputs video signals from all the lines (k lines) during the read period of $1/120$ [s] from the time T3 to the time T4.

Then, each time a video signal output from each line of the image sensor 12e is input with regard to the imaging for the third frame, the storage control circuitry 14b temporarily stores a video signal output from each line in the memory circuitry 14g. Here, with regard to the imaging for the third frame, a video signal output from each line, sequentially from the first line to the last line, is stored in the memory circuitry 14g from the time T3 to the time T4. In this manner, video signals stored with regard to the imaging for the third frame are stored in the memory circuitry 14g until at least a time T7.

Here, an explanation is given of a process indicated by "(W2+IR2)+(IR1+IR3)/2" in FIG. 2. In the phase at the time T3, the memory circuitry 14g stores the video signal (IR1) of the first frame and the video signal (W2+IR2) of the second frame. As described above, the video signal (IR3) of the third frame starts to be stored in the memory circuitry 14g at the time T3.

According to the present embodiment, the imaging apparatus 10 synthesizes the video signal (IR1) of the first frame, the video signal (W2+IR2) of the second frame, and the video signal (IR3) of the third frame and outputs it to the display 101.

Here, an explanation is simply given of a case where, each time the video signal (IR3) is output from each line of the image sensor 12e with regard to the imaging for the third frame, the imaging apparatus 10 synthesizes the video signal (IR3) output from each line, the video signal (IR1) output from each line, and the video signal (W2+IR2) output from each line of the image sensors 12c to 12e and outputs a synthesis image to the display 101. In this case, a synthesis image of video signals output from all the lines is output to the display 101 in $1/120$ [s].

There is a period where no video signals are output to the display 101 during $1/120$ [s] from when a video signal of the last line is output to the display 101 with regard to the imaging for a certain frame until a video signal of the first line is output to the display 101 with regard to the imaging for the subsequent frame. A period where no video signals are output is also a period where the image presented on the display 101 is not updated. For this reason, the period of $1/120$ [s] where an image is updated and the period of $1/120$ [s] where an image is not updated are alternately arranged. In this case, as an image is not updated at a constant frequency, it is sometimes difficult for the display 101 to be responsive to these inputs.

According to the present embodiment, for updates to an image at a constant frequency, the frame rate of video signals of one frame output from the output circuitry 14e to the display 101 is set to 60 [fps]. That is, there is a reduction in the period from the output of a video signal of the last line with regard to the imaging for a certain frame until the output of a video signal of the first line with regard to the imaging for the subsequent frame.

Therefore, the storage control circuitry 14b sequentially reads, from the memory circuitry 14g, the video signal (IR1) output from each line with regard to the imaging for the first frame, the video signal (W2+IR2) output from each line with regard to the imaging for the second frame, and the video signal (IR3) output from each line with regard to the imaging for the third frame at the interval of $1/(60k)$ [s] from the time T3. For example, the storage control circuitry 14b reads the video signal (IR1) and the video signal (IR3) output from the m-th line of the image sensor 12e and the video signal (W2+IR2) output from the m-th line of the image sensors 12c to 12e. Here, m is a positive integer. Then, the storage control circuitry 14b outputs, to the image processing circuitry 14c, the video signal (IR1) and the video signal (IR3) output from the m-th line of the image sensor 12e and the video signal (W2+IR2) output from the m-th line of the image sensors 12c to 12e.

Then, the image processing circuitry 14c performs various types of image processing on the video signal (IR1) and the video signal (IR3) output from the m-th line of the image sensor 12e and the video signal (W2+IR2) output from the m-th line of the image sensors 12c to 12e and outputs it to the image synthesis circuitry 14d.

Specifically, the image processing circuitry 14c masks the images obtained in accordance with the video signals output from the line 42 and the line 43 described above. The image processing circuitry 14c sets the area of the image obtained in accordance with the video signal output from the line 44 described above as an effective image area.

Figure 3:
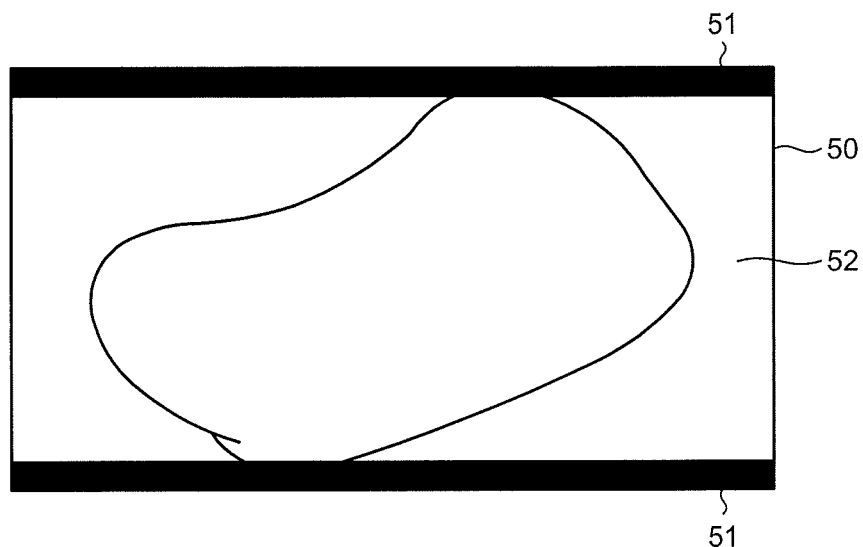
FIG. 3 is a diagram that illustrates an example of image processing conducted by image processing circuitry according to the embodiment.

FIG. 3 is a diagram that illustrates an example of image processing conducted by the image processing circuitry 14c. As illustrated in the example of FIG. 3, for example, the image processing circuitry 14c generates a color image 50 in which the images obtained in accordance with the video signals (W2+IR2) output from the line 42 and the line 43 described above are replaced with images 51 in black and the area of the image obtained in accordance with the video signal (W2+IR2) output from the line 44 described above is set as an effective image area 52. Here, the video signal (W2+IR2) or the color image 50 corresponds to a first image.

The color image 50 illustrated in the example of FIG. 3 is an example of the color image in a case where the pixels of the image sensors 12c to 12e receive light during only the period that is centered on the blanking period 40 and is obtained by adding 1/1200 [s] to the blanking period 40. On the color image 50, 10% of the entire area of the color image 50 is masked.

In the same manner, the image processing circuitry 14c generates a fluorescence image in which the images obtained in accordance with the video signals (IR1) output from the line 42 and the line 43 described above are replaced with black images and the area of the image obtained in accordance with the video signal (IR1) output from the above-described line 44 is set as an effective image area. The image processing circuitry 14c generates a fluorescence image in which the images obtained in accordance with the video signals (IR3) output from the line 42 and the line 43 described above are replaced with black images and the area of the image obtained in accordance with the video signal (IR3) output from the above-described line 44 is set as an effective image area. Here, the video signal (IR1), the video signal (IR3), or the fluorescence image correspond to a second image.

The image synthesis circuitry 14d synthesizes the video signal (IR1) output from each line of the image sensor 12e with regard to the imaging for the first frame and the video signal (IR3) output from each line of the image sensor 12e with regard to the imaging for the third frame to generate a synthesis image. For example, the image synthesis circuitry 14d synthesizes the video signal (IR1) and the video signal (IR3) to generate a synthesis image ((IR1+IR3)/2).

Then, the image synthesis circuitry 14d extracts for example part of the synthesis image ((IR1+IR3)/2) with luminance more than a threshold. Then, the image synthesis circuitry 14d generates a marker that has the same position and area as the extracted part and that has a predetermined color (e.g., highly intense green) assigned thereto. Then, the image synthesis circuitry 14d superimposes the generated marker on the video signal (W2+IR2) output from each line with regard to the imaging for the second frame to generate a synthesis image (W2+IR2+(IR1+IR3)/2). Then, the image synthesis circuitry 14d outputs the generated synthesis image (W2+IR2+(IR1+IR3)/2) to the output circuitry 14e. The image synthesis circuitry 14d generates a synthesis image by using a color image and multiple (two) fluorescence images generated before and after the color image.

For example, the color tone of a color image obtained as an in-vivo image of the subject 100 is a reddish color tone in whole. For this reason, if red is assigned to a marker, for example, the marker is not noticeable. Therefore, green that is a complementary color of red is assigned to the marker so that the marker is noticeable.

Instead of the marker, the image synthesis circuitry 14d may extract an outline component from a fluorescence image obtained due to fluorescence and superimpose the extracted outline component on a color image to generate a synthesis image.

The image synthesis circuitry 14d performs the above process on video signals output from all the lines. Specifically, the image synthesis circuitry 14d outputs a synthesis image of video signals output from all the lines to the output circuitry 14e during the period of 1/60 [s] from the time T3 to the time T5. Thus, as indicated by "W2+IR2+(IR1+IR3)/2" in FIG. 2, the output circuitry 14e outputs a synthesis image of video signals from all the lines to the display 101 during the period of 1/60 [s] from the time T3 to the time T5. Hence, the synthesis image presented on the display 101 is updated at the interval of 1/60 [s].

For the fourth and subsequent frames, imaging operation is repeatedly conducted in the same manner as the imaging operation described with regard to the imaging for the first frame, the imaging for the second frame, and the imaging for the third frame. Therefore, the control circuitry 14a causes the light source device 30 to continuously output excitation light and causes the light source device 30 to output white light once in two frames in synchronization with the blanking period 40 or the blanking peripheral period 41. The image processing circuitry 14c generates a fluorescence image in accordance with video signals generated by the pixels of the image sensor 12e after receiving fluorescence based on excitation light. Video signals generated by the pixels of the image sensor 12e after receiving fluorescence are an example of a first electric signal.

The image processing circuitry 14c generates a color image in accordance with video signals generated by the pixels of the image sensors 12c to 12e after simultaneously receiving fluorescence and white light. Video signals generated by the pixels of the image sensors 12c to 12e after simultaneously receiving fluorescence and white light are an example of a second electric signal.

The image synthesis circuitry 14d uses a fluorescence image and a color image to generate a synthesis image. For example, the image processing circuitry 14c and the image synthesis circuitry 14d are an example of an image generating unit.

Figure 4:
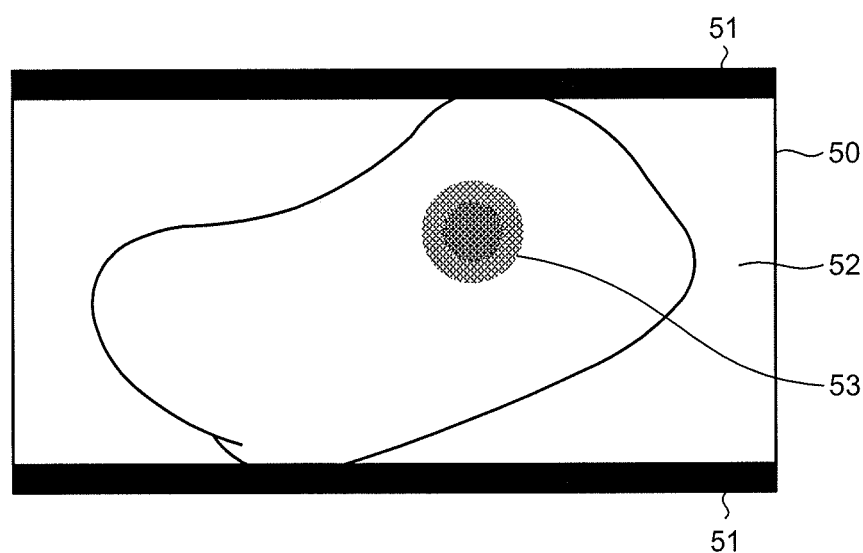
FIG. 4 is a diagram that illustrates an example of a synthesis image according to the embodiment.

FIG. 4 is a diagram that illustrates an example of the synthesis image. FIG. 4 illustrates an example of the synthesis image in which a marker 53 is superimposed on the color image 50 where part that is likely to have uneven brightness is masked. This allows users to easily observe for example the marker 53 that is a notable area. It is possible for users to obtain information on the marker 53 while observing the color image 50 that is a color image with content that is actually recognizable by persons.

With regard to the color image 50, the exposure timing is identical. Therefore, with the imaging apparatus 10 according to the present embodiment, the occurrence of image distortion may be prevented. Thus, with the imaging apparatus 10 according to the present embodiment, it is possible to ensure the image quality sufficient for observation for users such as doctors who observe an image.

As illustrated in FIG. 4, the image processing circuitry 14c sets, in the synthesis image, the effective image area 52 except for at least the synthesis image's edge portions corresponding to the first line and the last line. The image processing circuitry 14c and the image synthesis circuitry 14d generate the synthesis image where the area other than the effective image area 52 is replaced with the black image (different image) 51.

Here, an explanation is given of a case where the imaging target moves in a predetermined direction on a synthesis image. Furthermore, an explanation is given of a case where the marker obtained from the fluorescence image (IR1) is superimposed on the color image (W2+IR2) to generate the synthesis image (W2+IR2+IR1). In this case, as the imaging target moves, the position of the center of gravity of the marker is located backward in terms of time relative to the position of the center of gravity of the imaging target rendered on the color image (W2+IR2).

Next, an explanation is given of a case where the marker obtained from the fluorescence image (IR3) is superimposed on the color image (W2+IR2) to generate the synthesis image (W2+IR2+IR3). In this case, as the imaging target moves, the position of the center of gravity of the marker is located forward in terms of time relative to the position of the center of gravity of the imaging target rendered on the color image (W2+IR2).

Here, according to the present embodiment, the marker obtained from the synthesis image ((IR1+IR3)/2) of the fluorescence image (IR1) and the fluorescence image (IR3) is superimposed on the color image (W2+IR2) to generate the synthesis image (W2+IR2+(IR1+IR3)/2). According to the present embodiment, even when the imaging target moves, the marker obtained from the synthesis image ((IR1+IR3)/2) of the fluorescence image (IR1) and the fluorescence image (IR3), which are captured at the previous imaging timing and the subsequent imaging timing with respect to the imaging timing of the color image (W2+IR2) by substantially the identical time, is superimposed on the color image (W2+IR2). For this reason, the difference between the position of the center of gravity of the color image (W2+IR2) and the position of the center of gravity of the synthesis image ((IR1+IR3)/2) is relatively small. Therefore, it is possible to reduce misalignment of the position of the center of gravity of the marker relative to the position of the center of gravity of the imaging target rendered on the synthesis image (W2+IR2+(IR1+IR3)/2). Thus, according to the present embodiment, it is possible to reduce the user's uncomfortable feeling caused by the synthesis image (W2+IR2+(IR1+IR3)/2) due to a movement.

The imaging operation in FIG. 2 has been described above. In the lighting pattern used for the imaging operation, the IR laser 30d constantly (continuously) outputs excitation light. Therefore, the amount of fluorescence received by the image sensor 12e is large as compared to a case where excitation light is not constantly output. This may improve the receiving sensitivity of fluorescence and may prevent a decrease in the luminance of a fluorescence image due to an insufficient amount of light.

Figure 5:
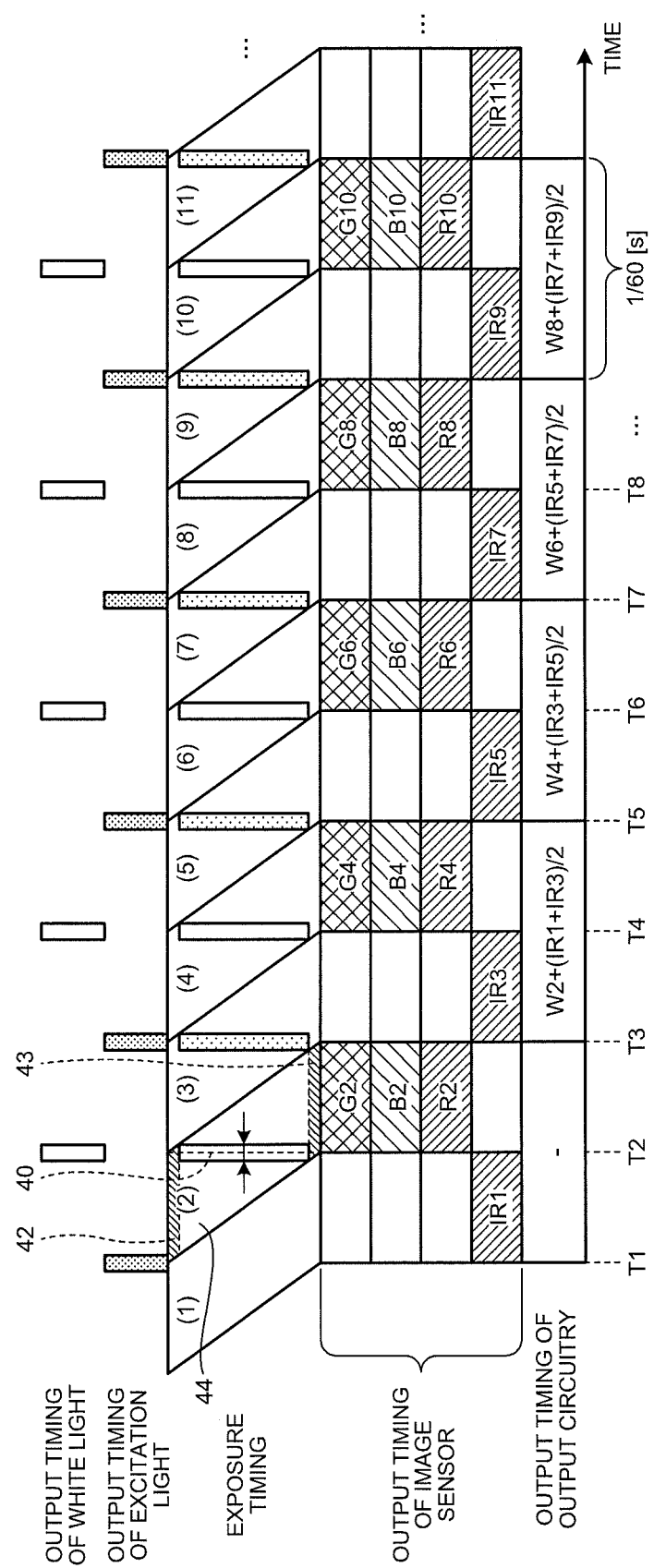
FIG. 5 is a diagram that illustrates an example of the imaging operation of the imaging apparatus according to the embodiment.

Next, with reference to FIG. 5, an explanation is given of the output pattern in a case where the amount of reflected light of white light output from the white LED 30b is substantially the same as the amount of fluorescence generated due to the emission of excitation light.

FIG. 5 is a diagram that illustrates an example of the imaging operation of the imaging apparatus 10. FIG. 5 illustrates the same timing chart as that in FIG. 2, although the output timing (output pattern) of excitation light is different.

Specifically, the control circuitry 14a outputs, to the timing-signal generation circuitry 14f, the control signal for outputting a second light-source control signal before the imaging for the first frame is started or when the imaging for the first frame is started. The second light-source control signal is a control signal for implementing the output pattern (second lighting pattern) that causes the IR laser 30d to output excitation light alternating with white light.

On the basis of the above-described control signal output from the control circuitry 14a, the timing-signal generation circuitry 14f outputs, to the drive circuitry 30c, the second light-source control signal for outputting excitation light for each odd-number frame. The drive circuitry 30c causes the IR laser 30d to output excitation light for each odd-number frame on the basis of the second light-source control signal output from the timing-signal generation circuitry 14f.

Here, the excitation light is output from the IR laser 30d during the blanking period 40 or the blanking peripheral period 41 in the same manner as white light. The output timing and the output time period of the excitation light are not particularly specified as long as they are within the blanking period 40 or the blanking peripheral period 41. For example, the excitation light may be continuously output during the blanking period 40 or the blanking peripheral period 41. The excitation light may be output one time at specific timing within the blanking period 40 or the blanking peripheral period 41, or the excitation light may be intermittently output during the blanking period 40 or the blanking peripheral period 41. For example, a configuration may be such that, in this lighting pattern, the excitation light is output in the order of the one-time output, the intermittent output, and then the continuous output or in the inverse order so that the amount of fluorescence generated due to the emission of the excitation light is changed.

As described above, in the output pattern of FIG. 5, the IR laser 30d outputs the excitation light alternating with the white light once in two frames. Therefore, the amount of fluorescence received by the image sensor 12e is smaller than that in the output pattern of FIG. 2.

With the imaging operation of FIG. 5, as no excitation light is output during the blanking period 40 or the blanking peripheral period 41 when a switchover is made from an odd-number frame to an even-number frame, a video signal of a fluorescence component is not included in an even-number frame. Therefore, for example, from the time T3 to the time T5, the output circuitry 14e synthesizes the video signal (IR1) of the first frame, the video signal (W2) of the second frame, and the video signal (IR3) of the third frame and outputs it to the display 101.

Figure 6:
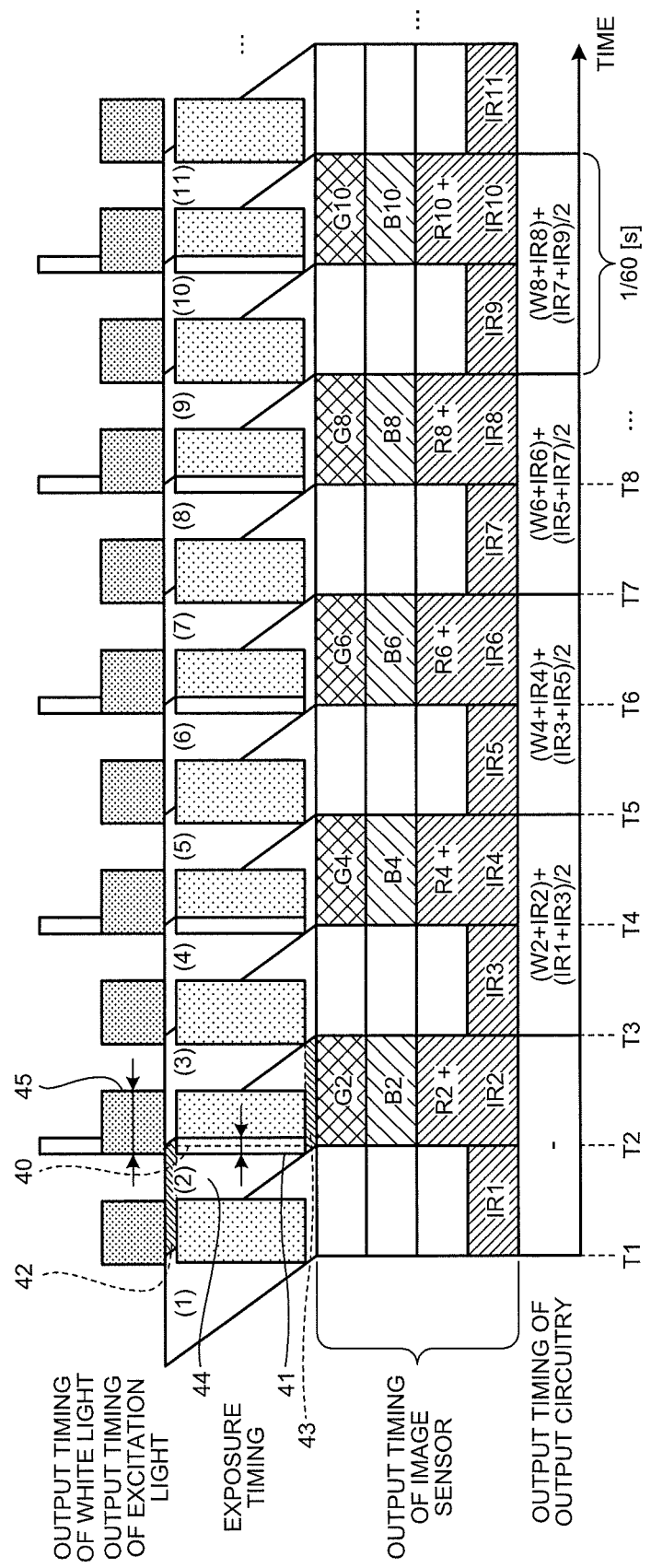
FIG. 6 is a diagram that illustrates an example of the imaging operation of the imaging apparatus according to the embodiment.

Next, with reference to FIG. 6, the output pattern is described in a case where the amount of fluorescence generated due to the emission of excitation light is smaller than the amount of reflected light of white light output from the white LED 30b, that is, in a case where the amount of fluorescence with respect to the amount of reflected light of white light is larger than the amount of fluorescence assumed in FIG. 2 and is smaller than the amount of fluorescence assumed in FIG. 5.

FIG. 6 is a diagram that illustrates an example of the imaging operation of the imaging apparatus 10. FIG. 6 illustrates the same timing chart as those in FIGS. 2 and 5, although the output timing (output pattern) of excitation light is different.

Specifically, the control circuitry 14a outputs, to the timing-signal generation circuitry 14f, the control signal for outputting a third light-source control signal before the imaging for the first frame is started or when the imaging for the first frame is started. The third light-source control signal is a control signal for implementing the output pattern (third lighting pattern) that causes the IR laser 30d to output excitation light for each frame.

On the basis of the above-described control signal output from the control circuitry 14a, the timing-signal generation circuitry 14f outputs, to the drive circuitry 30c, the third light-source control signal for outputting excitation light for each frame. The drive circuitry 30c causes the IR laser 30d to output excitation light for each frame on the basis of the third light-source control signal output from the timing-signal generation circuitry 14f.

In this output pattern, the period (an output period 45) for outputting the excitation light is not limited within the blanking period 40 or the blanking peripheral period 41, and the excitation light may be output in a range more than the blanking peripheral period 41 within the frame. Specifically, the output period 45 is variable in the range from the start time of the blanking period 40 or the blanking peripheral period 41 of the leading frame out of the successive two frames until immediately before the start time of the blanking period 40 or the blanking peripheral period 41 of the subsequent frame. It is assumed that the start time of the output period 45 is included in the blanking period 40 or the blanking peripheral period 41.

In the example of FIG. 6, the output of excitation light starts in the blanking period 40 or the blanking peripheral period 41 of each frame, and the output period 45 continues until the time beyond the blanking peripheral period 41 of the frame. A state where the output period 45 reaches the start time of the blanking period 40 or the blanking peripheral period 41 in the subsequent frame corresponds to a state where excitation light is constantly output (constantly turned on) as described in FIG. 2, and this means that the output pattern of FIG. 6 is changed to the output pattern of FIG. 2.

In this output pattern, the method for outputting the excitation light is not particularly specified as long as it is within the output period 45. For example, the excitation light may be continuously output during the output period 45.

The excitation light may be output one time at specific timing within the output period 45, or the excitation light may be intermittently output within the output period 45. For example, a configuration may be such that, in this lighting pattern, the excitation light is output in the order of the one-time output, the intermittent output, and then the continuous output or in the inverse order so that the amount of fluorescence generated due to the emission of the excitation light is changed.

As described above, in the lighting pattern illustrated in FIG. 6, the excitation light is output from the IR laser 30d for each frame. Therefore, the amount of fluorescence received by the image sensor 12e is smaller than the amount of fluorescence illustrated in FIG. 2 and is larger than the amount of fluorescence illustrated in FIG. 5.

With the imaging operation in FIG. 6, video signals output from the output circuitry 14e are the same as those in FIG. 2. Therefore, for example, from the time T3 to the time T5, the output circuitry 14e synthesizes the video signal (IR1) of the first frame, the video signal (W2+IR2) of the second frame, and the video signal (IR3) of the third frame and outputs it to the display 101.

Figure 7:
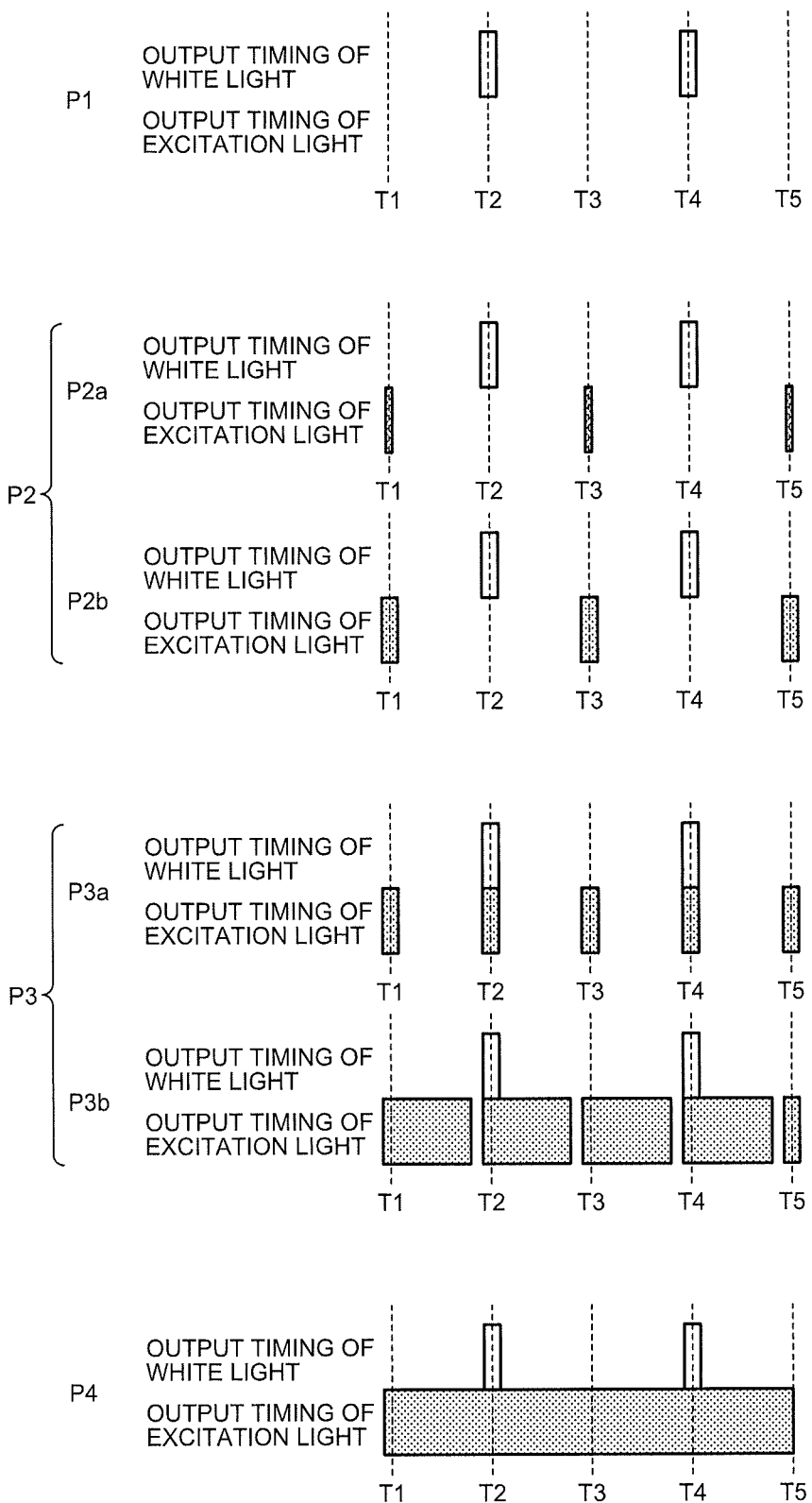
FIG. 7 is a diagram that illustrates output patterns according to the embodiment.

Next, with reference to FIG. 7, an explanation is given of the relationship among multiple output patterns including the output patterns described above in FIGS. 2, 5, and 6.

FIG. 7 is a diagram that illustrates output patterns. Patterns P1 to P4 schematically illustrate different output patterns of excitation light, and the horizontal axis indicates the time. The time T1 to the time T5 illustrated in the drawing correspond to the time T1 to the time T5 illustrated in FIGS. 2, 5, and 6. In the example illustrated, white light is output during the blanking period 40 or the blanking peripheral period 41 once in two frames (is output for each even-number frame) in the same manner as in FIGS. 2, 5, and 6.

First, the pattern P1 is, for example, a lighting pattern applied to output only white light. In the pattern P1, the excitation light is constantly turned off, and the image sensor 12e receives reflected light due to the white light. The pattern P1 corresponds to a fourth lighting pattern.

The pattern P2 corresponds to the output pattern of excitation light described in FIG. 5. In the pattern P2, the excitation light and the white light are alternately output in synchronization with the blanking period 40 or the blanking peripheral period 41. Here, if the pattern P1 and the pattern P2 are compared with each other, the total output period of excitation light in two frames in the pattern P2 is longer. Therefore, the amount of fluorescence received by the image sensor 12e in the pattern P2 is larger.

Furthermore, FIG. 7 illustrates a pattern P2a and a pattern P2b as the pattern P2. The pattern P2a is an output pattern for outputting excitation light during the blanking period 40, and the pattern P2b is an output pattern for outputting excitation light during the blanking peripheral period 41. If the pattern P2a and the pattern P2b are compared with each other, the output period of excitation light in the pattern P2b is longer. Therefore, the amount of fluorescence received by the image sensor 12e in the pattern P2b is longer than that in the pattern P2a.

The pattern P3 corresponds to the output pattern of excitation light described in FIG. 6. In the pattern P3, the excitation light is output for each frame in synchronization with the blanking period 40 or the blanking peripheral period 41. Here, if the pattern P2 and the pattern P3 are compared with each other, the total output period of excitation light in two frames in the pattern P3 is larger. Therefore, the amount of fluorescence received by the image sensor 12e in the pattern P3 is larger than that in the pattern P2. FIG. 7 illustrates a pattern P3a and a pattern P3b as lighting patterns of the pattern P3. The pattern P3a illustrates an example in which the output period 45 of excitation light is the blanking peripheral period 41, and the pattern P3b illustrates an example in which the output period 45 of excitation light is extended to the range beyond the blanking peripheral period 41. Here, if the pattern P3a and the pattern P3b are compared with each other, the total output period of excitation light in two frames in the pattern P3b is larger. Therefore, the amount of fluorescence received by the image sensor 12e in the pattern P3b is larger than that in the pattern P3a.

The pattern P4 corresponds to the lighting pattern of excitation light described in FIG. 2. In the pattern P4, excitation light is constantly (continuously) output. Therefore, if the pattern P3 and the pattern P4 are compared with each other, the total output period of excitation light in two frames in the pattern P4 is larger. Therefore, the amount of fluorescence received by the image sensor 12e in the pattern P4 is larger than that in the pattern P3.

As described above, the total output period of excitation light output from the IR laser 30d in two frames are different in the pattern P1 to the pattern P4. The total output period of excitation light output from the IR laser 30d in two frames is designed to increase from the pattern P1 to the pattern P4. Therefore, by operating the IR laser 30d while selectively using the pattern P1 to the pattern P4, the amount of fluorescence generated due to the emission of excitation light may be controlled.

Furthermore, the control circuitry 14a according to the present embodiment selectively uses the above-described output patterns to control the excitation light generated by the IR laser 30d such that the luminance of a fluorescence image becomes the target luminance with respect to the luminance of a color image. Specifically, the control circuitry 14a, in cooperation with the image processing circuitry 14c, or the like, selectively uses the output patterns to control the excitation light generated by the IR laser 30d so as to control the luminance of a fluorescence image. The target luminance is, for example, the value of luminance designated by a user.

Here, an example of the method for calculating the luminance of an image is described. The control circuitry 14a performs the following process for each frame. For example, the control circuitry 14a acquires, from the image processing circuitry 14c, the image data on each of a color image and a fluorescence image obtained as a result of various types of image processing. Then, the control circuitry 14a selects the highest luminance from the R luminance, the G luminance, and the B luminance of each pixel forming the image data on a pixel by pixel basis. For example, each pixel forming the image corresponds to each pixel of the image sensors 12c to 12e. The control circuitry 14a calculates the total of luminance selected for the pixels. Then, the control circuitry 14a divides the calculated total of luminance by the number of pixels forming the image to calculate the average value of luminance per pixel. Then, the control circuitry 14a treats the calculated average value of luminance as the luminance of the image.

The control circuitry 14a switches the output pattern regarding the control on the IR laser 30d on the basis of the luminance of the color image and the fluorescence image to control the luminance of the fluorescence image with respect to the color image. The control circuitry 14a, in cooperation with the image processing circuitry 14c, controls a gain amplification process (digital gain) with regard to the fluorescence image to control the luminance of the fluorescence image with respect to the color image.

Figure 8:
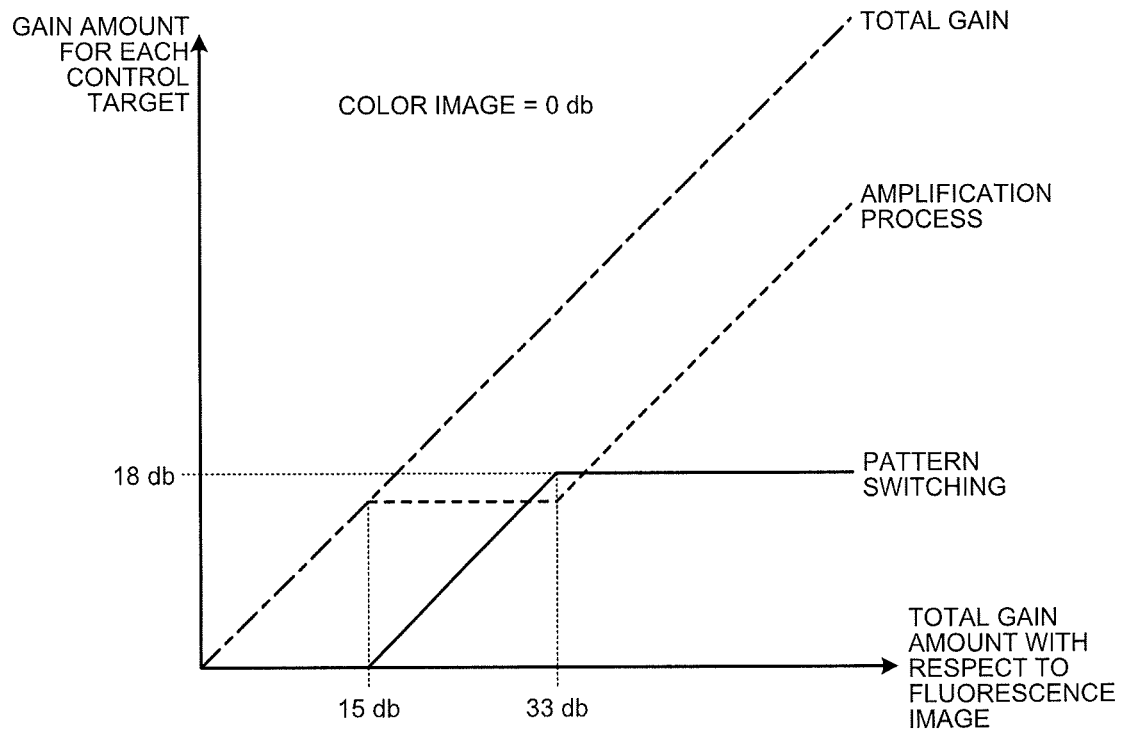
FIG. 8 is a graph that illustrates an example of the control performed by control circuitry according to the embodiment.
Figure 9:
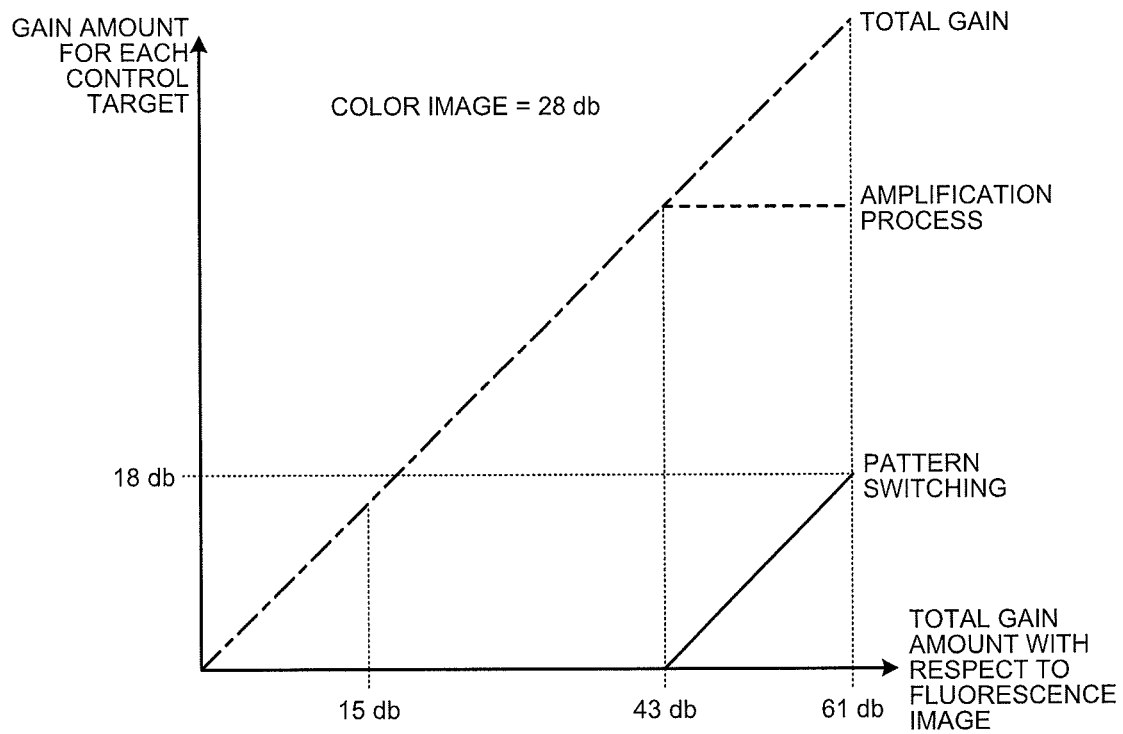
FIG. 9 is a graph that illustrates an example of the control performed by the control circuitry according to the embodiment.
Figure 10:
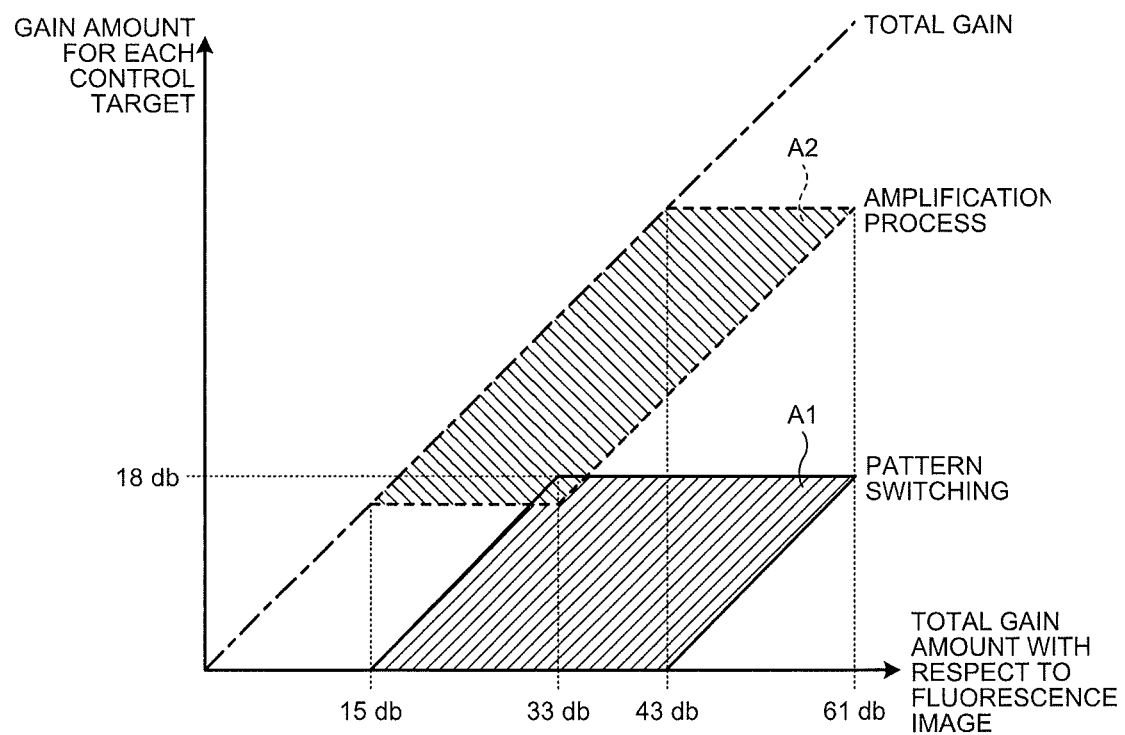
FIG. 10 is a graph that illustrates an example of the control performed by the control circuitry according to the embodiment.

With reference to FIGS. 8 to 10, the control on the luminance of a fluorescence image performed by the control circuitry 14a is described. FIGS. 8 to 10 are graphs that illustrate an example of the control performed by the control circuitry 14a. The horizontal axis indicates the total gain amount with regard to the fluorescence image, and the vertical axis indicates the gain amount of each control target (a lighting pattern, the image processing circuitry 14c). Here, for example, the amount of light (the light intensity× the output period) in the pattern P2b described in FIG. 7 is 0 dB, the amount of light in the pattern P4 is approximately 18 dB, and the output period in each pattern is represented as gain. The total gain amount with regard to the fluorescence image refers to the total value of the set value (amplification factor) for a gain amplification process by the image processing circuitry 14c and the gain relatively derived from the output period of excitation light.

The graph (pulse width adjustment) indicated by the solid line represents a change in the gain of the fluorescence image in accordance with the switching of the output pattern. The graph (amplification process) indicated by the dashed line represents a change in the gain of the fluorescence image in accordance with a gain amplification process. The graph (total gain) indicated by the dashed-dotted line corresponds to the total gain to obtain the target value of the luminance of the fluorescence image. In the example illustrated in FIGS. 8 to 10, the control is performed such that the set value for the gain amplification process on the fluorescence image is higher than the set value for the gain amplification process on the color image by more than 15 dB. In this manner, the set value for the gain amplification process on the fluorescence image is higher than the set value for the gain amplification process on the color image by more than a predetermined value; thus, even when a fluorescence image is included in the color image, the amount of amplification of the included fluorescence image component may be reduced, whereby the image quality may be improved.

FIG. 8 illustrates an example of the control in a case where the set value for the gain amplification process on the color image is one-fold (0 dB). This control example is applied to a case where white light is sufficiently bright as, for example, the distance between the imaging apparatus 10 and the subject 100 is short.

First, the control circuitry 14a controls the IR laser 30d with the pattern P2 described in FIG. 7 so as to output the excitation light alternating with the white light. Here, in a case where the value of subtraction of the gain amplification process on the color image from the gain amplification process on the fluorescence image is less than 15 dB, the control circuitry 14a, in cooperation with the image processing circuitry 14c, preferentially uses the gain amplification process on the fluorescence image until the difference between the gain amplification process on the fluorescence image and the gain amplification process on the color image becomes 15 dB.

To further increase the luminance of the fluorescence image on which the gain amplification process has been performed to obtain 15 dB, the control circuitry 14a switches the pattern P2 described in FIG. 7 to the pattern P3 so that the excitation light is output for each frame. The control circuitry 14a increases the time length of the output period 45 as appropriate while the excitation light is output in the pattern P3. Accordingly, the total gain for the fluorescence image is increased. When the output period 45 reaches the start time of the blanking period 40 or the blanking peripheral period 41 of the subsequent frame, the control circuitry 14a switches to the pattern P4 described in FIG. 7 so that the excitation light is continuously output.

In FIG. 8, the control with the pattern P3 starts at the position where the total gain amount of the fluorescence image is 15 dB, and the time length of the output period 45 is gradually increased so that the gain is finally amplified by 18 dB. Therefore, the total gain of the fluorescence image when a switchover is made to the pattern P4 is 33 dB, 18 dB in addition to 15 dB.

To further increase the luminance of the fluorescence image whose gain has been amplified to 33 dB, the control circuitry 14a, in cooperation with the image processing circuitry 14c, performs the gain amplification process on the fluorescence image or a video signal (hereafter, collectively referred to as fluorescence image) that is the basis of the fluorescence image to amplify the total gain of the fluorescence image.

FIG. 9 illustrates an example of the control in a case where the gain amplification process on the color image is 28 dB. This control example is applied to a case where the set value for the gain amplification process on the color image is high as white light is dark due to, for example, the long distance between the imaging apparatus 10 and the subject 100.

First, the control circuitry 14a causes the IR laser 30d to output the excitation light in the pattern P2 in the same manner as in FIG. 8. Then, the control circuitry 14a, in cooperation with the image processing circuitry 14c, performs the gain amplification process as appropriate until the gain amplification process on the fluorescence image reaches 43 dB, i.e., 15 dB in addition to the gain amplification process (28 dB) on the color image.

To further increase the luminance of the fluorescence image on which the gain amplification process has been performed to obtain 43 dB, the control circuitry 14a switches the pattern P2 to the pattern P3 so that the excitation light is output for each frame. The control circuitry 14a increases the time length of the output period 45 as appropriate while the excitation light is output in the pattern P3. Accordingly, the total gain amount for the fluorescence image is increased. When the output period 45 reaches immediately before the start time of the blanking period 40 or the blanking peripheral period 41 of the subsequent frame, the control circuitry 14a switches to the pattern P4 described in FIG. 7 so that the excitation light is continuously output.

In FIG. 9, the control with the pattern P3 starts at the position where the total gain of the fluorescence image is 43 dB, and the time length of the output period 45 is gradually increased so that the gain is finally amplified by 18 dB. Therefore, the total gain of the fluorescence image when a switchover is made to the pattern P4 is 61 dB, i.e., 18 dB in-addition to 43 dB.

In FIG. 10, the control results of FIGS. 8 and 9 are overlapped. Here, a range A1 indicates the range of gain in the case of the amplification by changing the output period 45 with the pattern P3. A range A2 indicates the range of gain in the case of the amplification by the gain amplification process. Thus, according to the present embodiment, the luminance of the fluorescence image is controlled to be the target luminance by a combination of the amplification due to switching of an output pattern and the amplification due to a gain amplification process. Thus, the use of a gain amplification process may be reduced, and therefore a noise component included in a fluorescence image may be decreased. Furthermore, a fluorescence image component included in a color image may be reduced, and therefore a high image quality may be achieved.

Here, an example of the gain amplification process performed by the image processing circuitry 14c is described. For example, during the imaging for the first frame, the image processing circuitry 14c performs the gain amplification process for a fluorescence image on the video signal (IR1) output from the m-th line of the image sensor 12e. In the same manner, during the imaging for the third frame, the image processing circuitry 14c performs the gain amplification process for a fluorescence image on the video signal (IR3) output from the m-th line of the image sensor 12e.

During the imaging for the second frame, the image processing circuitry 14c performs the gain amplification process for a color image on the m-th video signal (W2+IR2) without performing the gain amplification process for a fluorescence image.

In the above-described control example, the output pattern to be used is selected based on the difference between the set value for the gain amplification process for a color image and the set value for the gain amplification process for a fluorescence image; however, this is not a limitation, and the output pattern to be used may be selected based on the ratio between the set value for the gain amplification process for a color image and the set value for the gain amplification process for a fluorescence image.

Figure 11:
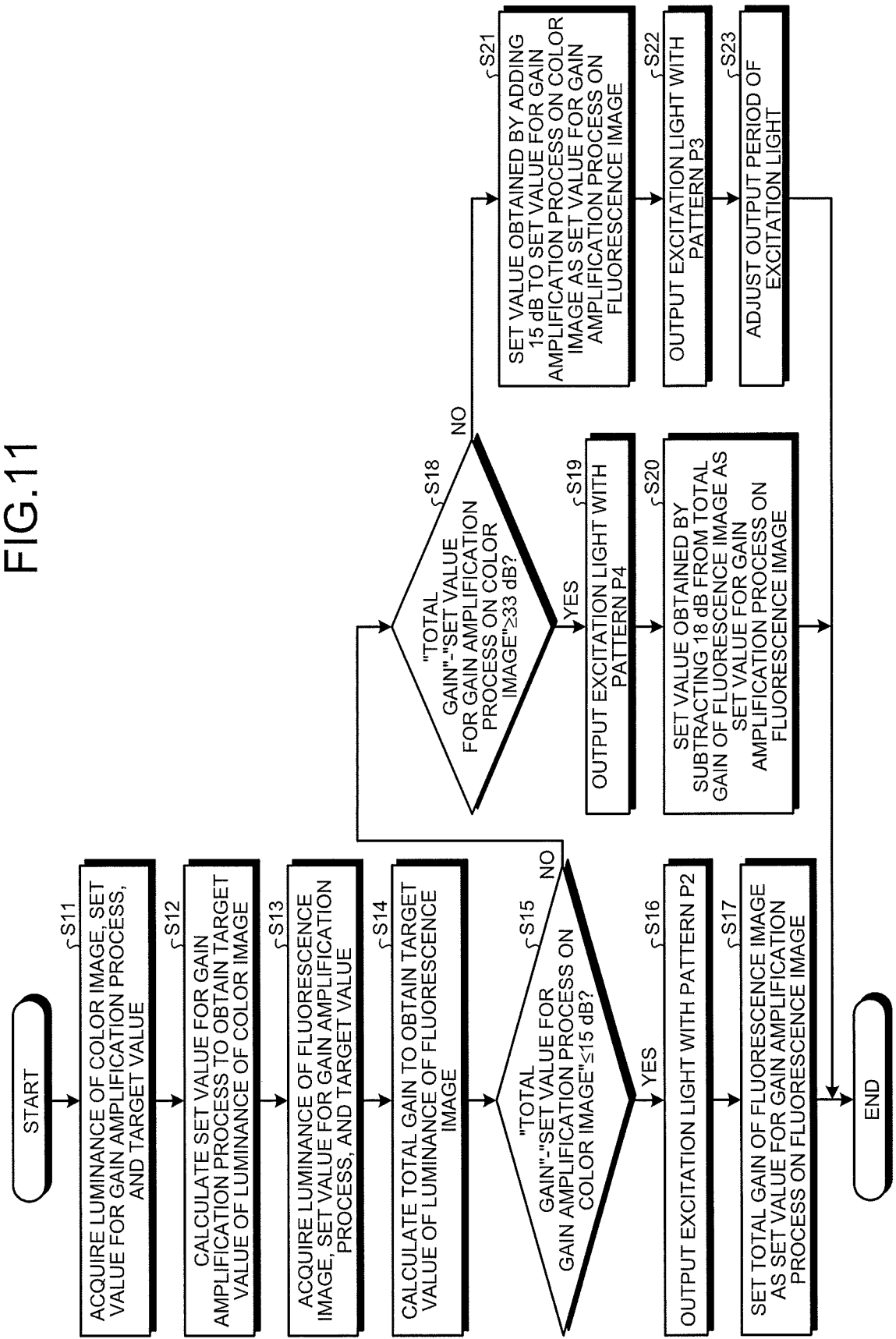
FIG. 11 is a flowchart that illustrates an example of a process performed by the control circuitry according to the embodiment.

Next, a process regarding the control on the luminance of a fluorescence image performed by the control circuitry 14a is described. FIG. 11 is a flowchart that illustrates an example of a process performed by the control circuitry 14a. This process is performed by the control circuitry 14a when a command for starting to capture the inside of the subject 100 is input to the CCU 14 by an input device that receives commands from a user, such as an undepicted mouse or keyboard. The process in FIG. 11 is based on the above-described control example in FIG. 8.

First, the control circuitry 14a acquires the current luminance of the color image, the current set value for the gain amplification process on the color image, and the target value of the luminance of the color image (Step S11). Then, the control circuitry 14a calculates the set value for the gain amplification process to obtain the target value of the luminance of the color image on the basis of the luminance of the color image and the target value acquired at Step S11 (Step S12).

Then, the control circuitry 14a acquires the current luminance of the fluorescence image, the current set value for the gain amplification process on the fluorescence image, and the target value of the luminance of the fluorescence image (Step S13). Then, the control circuitry 14a calculates the total gain (corresponding to the dashed-dotted line in FIG. 8) to obtain the target value of the luminance of the fluorescence image on the basis of the luminance of the fluorescence image and the target value acquired at Step S13 (Step S14).

Then, the control circuitry 14a determines whether the value obtained by subtracting the set value for the gain amplification process on the color image calculated at Step S12 from the total gain of the fluorescence image calculated at Step S14 is equal to or less than 15 dB (Step S15). Here, when it is determined that it is equal to or less than 15 dB (Step S15; Yes), the control circuitry 14a causes the IR laser 30d to output the excitation light with the pattern P2 (Step S16). Then, the control circuitry 14a sets the total gain of the fluorescence image as the set value for the gain amplification process on the fluorescence image (Step S17).

When it is determined that it is more than 15 dB (Step S15; No), the control circuitry 14a determines whether the value obtained by subtracting the set value for the gain amplification process on the color image calculated at Step S12 from the total gain of the fluorescence image calculated at Step S14 is equal to or more than 33 dB (Step S18). Here, when it is determined that it is equal to or more than 33 dB (Step S18; Yes), the control circuitry 14a causes the IR laser 30d to output the excitation light with the pattern P4 (Step S19). Then, the control circuitry 14a sets the value obtained by subtracting 18 dB from the total gain of the fluorescence image as the set value for the gain amplification process on the fluorescence image (Step S20).

When it is determined that it is less than 33 dB at Step S18 (Step S18; No), the control circuitry 14a sets the value obtained by adding 15 dB to the set value for the gain amplification process on the color image as the set value for the gain amplification process on the fluorescence image (Step S21). Then, the control circuitry 14a causes the IR laser 30d to output the excitation light with the pattern P3 (Step S22) and then adjusts the output period of the excitation light such that the value of the total gain of the fluorescence image becomes the value of the total gain calculated at Step S14 (Step S23).

The imaging apparatus 10 according to the present embodiment has been described above. With the imaging apparatus 10 according to the present embodiment, the IR laser 30d is controlled by selectively using multiple output patterns in which the total lighting period in two frames is different so that the luminance of a fluorescence image with respect to a color image may be adjusted; thus, it is possible to ensure the image quality sufficient for the user's observation. Furthermore, as a gain amplification process may be reduced, an improvement in the image quality may be achieved.

Modification 1

In the description according to the above embodiment, the output pattern is automatically selected under the control of the control circuitry 14a; however, this is not a limitation, and the output pattern may be manually selected according to a modification 1. In this case, according to the modification 1, for example, when a command for switching the output pattern is input to the CCU 14 from an input device, which receives commands from a user, such as an undepicted mouse or keyboard, the output pattern may be switched by the control circuitry 14a in accordance with the command.

Thus, the user switches the output pattern while checking the luminance of the fluorescence image with respect to the color image so as to obtain the fluorescence image with the desired luminance; thus, the image quality sufficient for the observation may be ensured.

Modification 2

In the description according to the above-described embodiment, the gain of the fluorescence image is amplified by using the image processing circuitry 14c; however, this is not a limitation, and the gain may be amplified by the image sensor 12e according to a modification 2. Thus, the same advantage as that in the above-described embodiment may be produced.

Modification 3

In the description according to the above-described embodiment, the example is explained in which the control circuitry 14a causes the white LED 30b to be turned on once in two frames in synchronization with the first period based on the blanking period 40, and causes the IR laser 30d to be turned on by selectively using multiple lighting patterns in which lighting timing is set in synchronization with the first period and the total lighting period in the two frames is different.

However, the control circuitry 14a causes the white LED 30b to be turned on M (M is an integer equal to or less than N (N is an integer equal to or more than two)) times in N frames in synchronization with the first period based on the blanking period 40, and causes the IR laser 30d to be turned on by selectively using multiple lighting patterns in which lighting timing is set in synchronization with the first period and the total lighting period in the N frames is different.

For example, in a first lighting pattern, the control circuitry 14a may cause the IR laser 30d to be constantly turned on during the N frames.

In a second lighting pattern, the control circuitry 14a may cause the IR laser 30d to be turned on alternating with the white LED 30b M times in the N frames in synchronization with the first period.

In a third lighting pattern, the control circuitry 14a may cause the IR laser 30d to be turned on for each frame in synchronization with the first period. In this case, the control circuitry 14a may variably control a lighting period for turning on the IR laser 30d in a range after a start time of the first period of a leading frame out of the N frames until immediately before a start time of the first period of a subsequent frame.

In a fourth lighting pattern, the control circuitry 14a may cause the IR laser 30d to be turned off during the N frames.

With the imaging apparatus according to the above-described embodiment or modification, it is possible to ensure the image quality sufficient for the user's observation.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An imaging apparatus comprising:
   a first light source that emits first light;
   a second light source that emits second light having a wavelength band that is partly or wholly different from a wavelength band of the first light;
   an image sensor that includes a plurality of pixels arranged in a matrix to receive light from an object irradiated with the first light and the second light, reads an electric signal generated by a pixel with a rolling shutter type, and outputs the electric signal for each frame; and
   control circuitry that
      causes the first light source to be turned on M times in N frames in synchronization with a first period based on a blanking period of the each frame, wherein M is an integer equal to or less than N, N is an integer equal to or more than two, and
      causes the second light source to be turned on by selectively using multiple lighting patterns in which lighting timing is set in synchronization with the first period and a total lighting period in the N frames is different.

2. The imaging apparatus according to claim 1, wherein, in a first lighting pattern, the control circuitry causes the second light source to be constantly turned on during the N frames.

3. The imaging apparatus according to claim 1, wherein, in a second lighting pattern, the control circuitry causes the second light source to be turned on alternating with the first light source M times in the N frames in synchronization with the first period.

4. The imaging apparatus according to claim 1, wherein, in a third lighting pattern, the control circuitry causes the second light source to be turned on for each frame in synchronization with the first period.

5. The imaging apparatus according to claim 4, wherein the control circuitry variably controls a lighting period for turning on the second light source in a range after a start time of the first period of a leading frame out of the N frames until immediately before a start time of the first period of a subsequent frame.

6. The imaging apparatus according to claim 1, wherein, in a fourth lighting pattern, the control circuitry causes the second light source to be turned off during the N frames.

7. The imaging apparatus according to claim 1, wherein the control circuitry selects any one of the multiple lighting patterns based on a luminance of a first image based on the first light received by the image sensor, a luminance of a second image based on the second light received by the image sensor, and a lighting period of the second light source corresponding to the second image.

8. The imaging apparatus according to claim 7, wherein the control circuitry selects any one of the lighting patterns based on a difference or a ratio between a first amplification factor of an amplification circuitry that amplifies the first light corresponding to the luminance of the first image and a second amplification factor of the amplification circuitry that amplifies the second light corresponding to the luminance of the second image.

9. The imaging apparatus according to claim 1, wherein the control circuitry switches the multiple lighting patterns in accordance with a command.

10. The imaging apparatus according to claim 1, wherein the first light is visible light, and the second light is excitation light of a fluorescence component.

11. A control method controlling an imaging apparatus including an image sensor, the image sensor
including a plurality of pixels arranged in a matrix to receive light from an object irradiated with first light and second light, the second light having a wavelength band that is partly or wholly different from a wavelength band of the first light,
reading an electric signal generated by a pixel with a rolling shutter type, and
outputting the electric signal for each frame, the control method comprises:
causing the first light to be emitted M times in N frames in synchronization with a first period based on a blanking period of the each frame, wherein M is an integer equal to or less than N, N is an integer equal to or more than two; and
causing the second light to be emitted by selectively using multiple lighting patterns in which lighting timing is set in synchronization with the first period and a total lighting period in the N frames is different.

* * * * *